United States Patent

Mims, Jr().

[11] 4,114,621
[45] Sep. 19, 1978

[54] COMBINATION INCONTINENT GARMENT AND LINER

[76] Inventor: Carl C. Mims, Jr., 311 Brainard Ave., Fayetteville, N.C. 28301

[21] Appl. No.: 748,319

[22] Filed: Dec. 7, 1976

[51] Int. Cl.² ........................................... A61F 13/16
[52] U.S. Cl. ..................................... 128/288; 128/2 F
[58] Field of Search ........... 128/284, 287, 288, 290 R, 128/290 H, 288, 2 F; 2/402, 408, 67

[56] References Cited

U.S. PATENT DOCUMENTS

| | | | |
|---|---|---|---|
| 1,494,044 | 5/1924 | Ward et al. | 128/288 |
| 2,258,502 | 10/1941 | Perez | 2/402 X |
| 2,277,043 | 3/1942 | Cohn | 128/284 |
| 2,348,242 | 5/1944 | Bullinger | 2/402 |
| 2,552,875 | 5/1951 | Stein | 2/408 |
| 2,575,701 | 11/1951 | Artzt | 2/402 |
| 2,681,032 | 6/1954 | Shaw | 128/284 X |
| 2,834,348 | 5/1958 | Tucci | 128/288 |
| 3,145,394 | 8/1964 | Melton | 2/402 |
| 3,322,122 | 5/1967 | Daniel | 128/284 |
| 3,828,785 | 8/1974 | Gamm | 128/288 |

*Primary Examiner*—Lawrence W. Trapp
*Attorney, Agent, or Firm*—Mills & Coats

[57] ABSTRACT

An incontinent garment which can be easily put on and removed from a wearer by one attendant. This garment is combined with a special disposable or semi-disposable liner which includes provisions for urological and stool testing means. The liner also includes a wick type indicator to alert an attendant when the liner has come soiled. The liner portion of the present invention additionally is so shaped as to provide form fitting comfort for the wearer and yet prevents leakage which could soil the supportive pants and ambient bed clothes.

6 Claims, 7 Drawing Figures

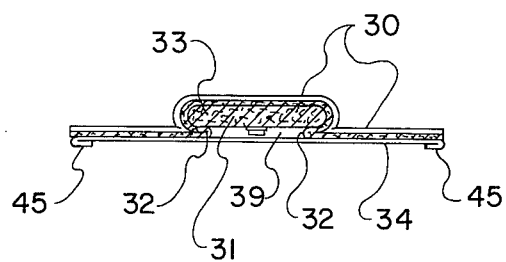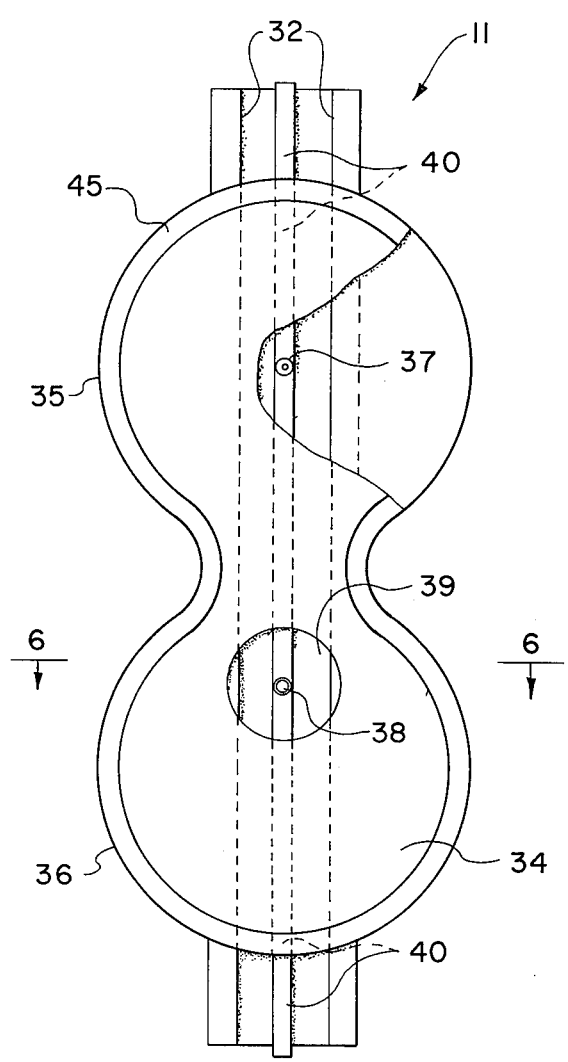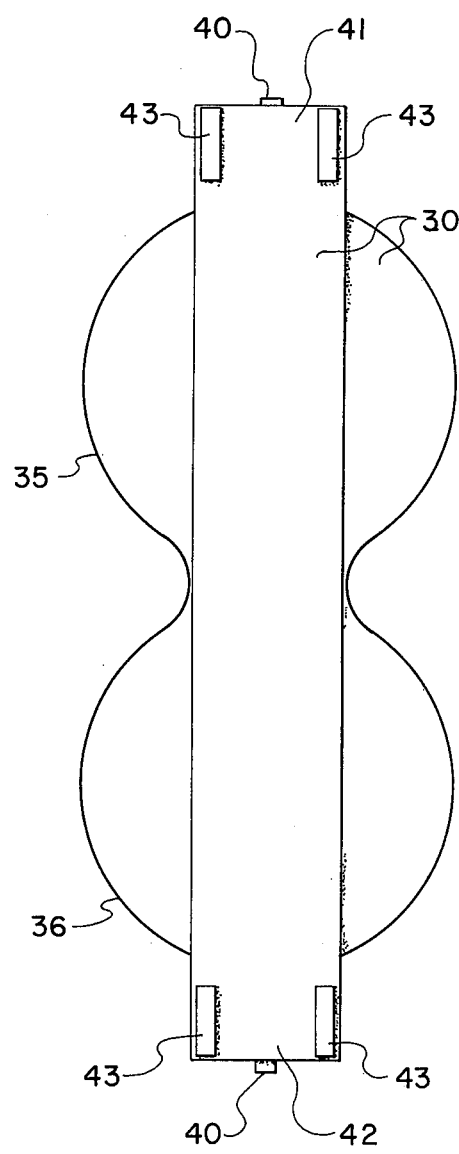

COMBINATION INCONTINENT GARMENT AND LINER

This invention relates to garments and more particularly to easily changeable incontinent pant type garments with a unique disposable liner having provisions for sampling devices and dampness condition indicators.

In the past various types of garments have been devised for incontinent type patients. These garments have included baby diaper type rubber pants which are tight around the legs, snapped on the sides, and have either disposable or washable liners. Additionally numerous washable and disposable sanitary napkin type garments have been developed for use with both normally active people as well as incontinents.

As a practical matter, most persons who are unable to get up out of bed to go to the bathroom have had a night shirt type garment placed on them and when they become soiled through either urine, stools or both, the garment as well as the ambient sheets, blankets and other bed clothes are removed and replaced. Because of the time involved in such a change of clothing and linens, the person is often allowed to remain in a soiled condition for a considerable period of time which is not only uncomfortable but very degrading. Additionally the wearing of either a diaper type garment, a night shirt type garment, or both are very degrading to the patient and often the private areas of the body are inadvertently exposed which is even more embarrassing.

After much research and study into the above mentioned problems, the present invention has been developed which can easily be placed on and removed from a person with very little effort and without requiring two attendants to accomplish the same. Additionally, the present invention includes a preferably disposable liner with provisions for connecting testing devices thereto. This liner also includes an indicating means when the same becomes soiled so that a quick and early change can be accomplished. Further, because of the unique design of the liner of the present invention, leakage is for all practical purposes eliminated while the comfort of the patient is maintained and even greatly improved from prior known liners.

In view of the above, it is an object of the present invention to provide an incontinent garment which is readily donnable and removable with a minimum disturbance to the wearer thereof.

Another object of the present invention is to provide an incontinent garment of the boxer short type.

Another object of the present invention is to provide an incontinent garment which includes a padded area for preventing or reducing development of bed sores.

A further object of the present invention is to provide an incontinent garment which includes pad means which prevents or reduces development of bed sores and additionally maintain the garment in normal wearing position and prevents the edges thereof from "creeping up".

An even further object of the present invention is to provide an incontinent garment which can easily and readily be changed on an incapacitated person by a single attendant.

Another object of the present invention is to provide, in combination with an incontinent garment, a preferably disposable liner with provision for testing devices incorporated thereinto.

Another object of the present invention is to provide, in combination with an incontinent garment, a liner with a visible indicating means to alert attendants when the same is soiled and needs changing.

Another object of the present invention is to provide, in a liner for an incontinent garment, a lip means about the periphery of the liner to prevent undesirable liquid seepage.

Another object of the present invention is to provide an incontinent garment liner which is so shaped to prevent bunching in the crotch area and yet has adequate absorbing volume to accommodate normal bowl and urine excretions.

Another object of the present invention is to provide a combination incontinent garment and liner wherein the liner is readily removable for disposal when soiled and yet is firmly held in place when used.

Other objects and advantages of the present invention will become apparent and obvious from a study of the following description and the accompanying drawings which are merely illustrative of such invention.

IN THE DRAWINGS:

FIG. 4 is an inside partially cutaway plan view of the liner portion of the present invention;

FIG. 5 is an exterior plan view of such liner;

FIG. 6 is a sectional view taken through lines 6-6 of FIG. 4; and

Figures 2, 3:
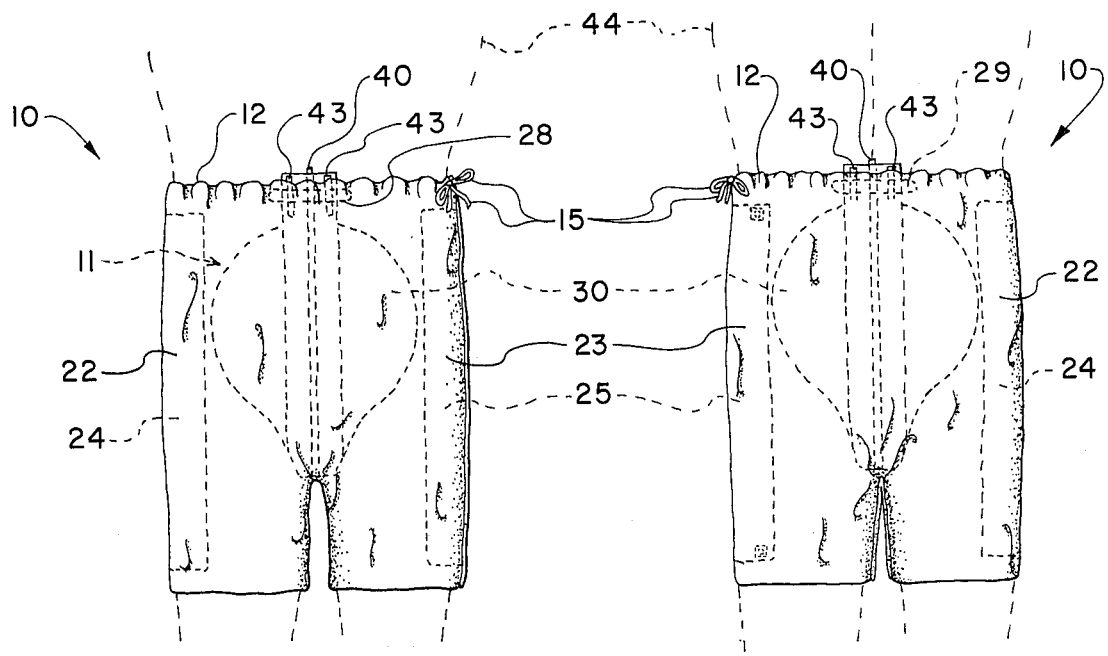
FIG. 2 is a normal front elevational view of the incontinent pants of the present invention showing the position of the liner when in use.
FIG. 3 is a normal rear elevational view taken from the side opposite FIG. 2.

With further reference to the drawings, the incontinent garment indicated generally at 10 is adapted to receive the liner indicated generally at 11.

Referring more specifically to the garment 10, a waistband 12 is provided which is in the form of a rolled upper portion of the garment 10. This rolled portion 13 can be held in place by any suitable means such as stitching 14. A tie or draw string 15 of any suitable material is provided and is passed through the slot formed in rolled portion 13 and when in use can be tied as seen clearly in FIGS. 2 and 3. This tie or draw string 15 can be secured at one point to the garment 10 by any suitable means (not shown) so that the same will not become lost or inadvertently slip out of the waistband slot within which it is disposed.

Figure 1:
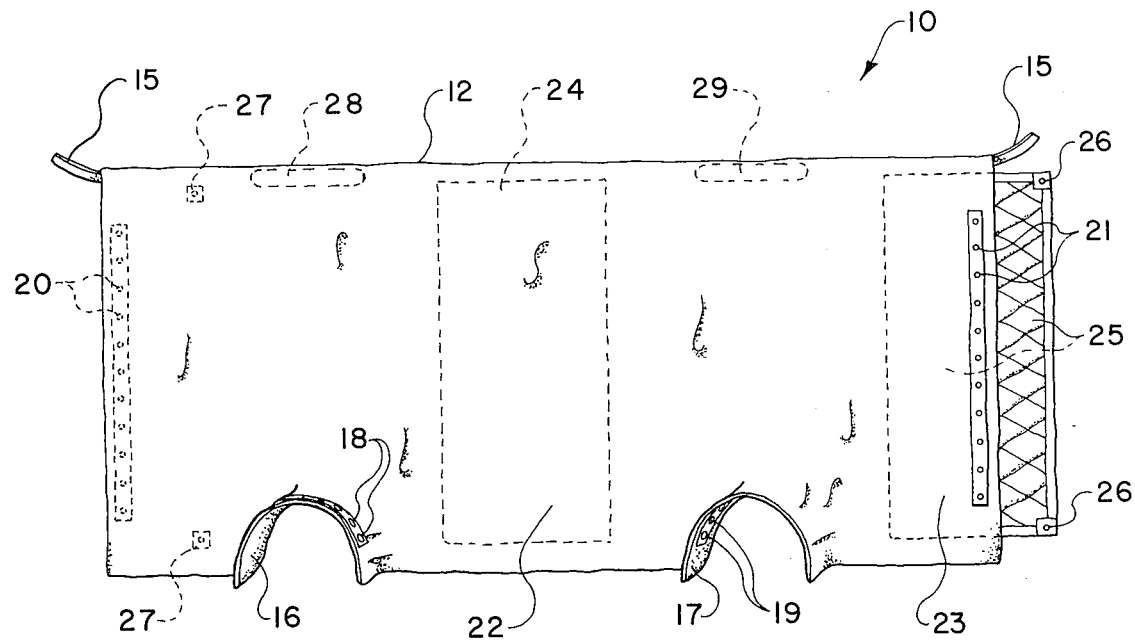
FIG. 1 is an outside perspective view of the incontinent garment of the present invention in open configuration.

The garment 10 of the present invention is generally flat in configuration when laid out as can clearly be seen in FIG. 1. This garment can be either formed from a reusable material such as cloth or it can be formed from a semi-disposable material such as Tyvek spunbonded olefin produced by DuPont Company and commercially available.

Two loop or arcuate portions form the crotch of the garment when in the use position. Opposed releasable fastening surfaces 18 and 19 are provided for securing the crotch portions 16 and 17 on the wearer of the garment. These securing means can be in any suitable form such as snaps, velcro type hook and loop fasteners, buttons or the like.

On opposed surfaces of opposite ends of the garment as seen in FIG. 1 are provided mateable securing surfaces 20 and 21. These fasteners can operate in the same manner as fasteners 18 and 19 of the crotch portions 16 and 17.

In the general area which forms the sides or hip portions 22 and 23 of the garment in the use configuration of FIGS. 2 and 3 are somewhat stiff pads 24 and 25. Because the garment 10 opens along the side for more convenient removal and donning, pad 25 includes a fastening means 26 at the corners thereof which overlaps the opposite end of the garment and which fasteners coordinate with mating fastener portions 27.

Relatively smooth contact areas 28 and 29 are provided adjacent the waistband portion 12 of the garment to receive the gummed or adhesive portions of the liner 11 as will hereinafter be described in more detail.

With specific reference to the liner 11, a backing 30 of plastic or other generally liquid impervious material is provided. This backing is somewhat wider than the finished liner product and is folded or tucked under as is seen clearly in FIG. 6. This configuration provides more absorbent area and a reservoir type pocket. A plurality of preferably four to six layers of filler 31 are provided and are composed of highly absorbent material such as paper stock. These filler layers are of generally the same size as the backing 30 and are folded over in the tucks 32 in adjacent conformity with the backing 30. Once the reservoir pocket 33 is thus formed with the adjacent layers of backing and filler, an inner surface 34 is placed thereover. This inner layer acts as a binder and is preferably made from a porous fiber material which by wick action will draw any moisture secreted by the wearer of the garment of the present invention inwardly away from such person and into the absorbent filler layers 31. This inner or binder layer conforms to the folded or tucked configuration of the backing 30 and thus presents a smooth surface to the body of the patient when in use. A lip 45 is provided about the periphery of the liner to further reduce the chance of leakage.

As can be seen in the drawings, particularly in FIG. 4, two rather large rounded areas 35 and 36 are provided to present added absorbent surfaces to be disposed adjacent the body of the wearer.

Not necessarily in the center of each of the circle portions 35 and 36 is provided a fastener 37 and 38, respectively, which can be in the form of female portion of a snap fastener although other coordinated fasteners could, of course, be used. A mating fastener portion (not shown) can be used to attach devices such as urological testers, tablet holders for detecting blood in stools and similar types of apparatus. If these or similar apparatus (not shown) are not used, then the liner can be used without the same and functions equally well. Also if desired, an opening such as that seen at 39 can be provided in the inner layer 34 and even through part or all of the absorbent filler layers 31 so that the apparatus referred to above can be more readily accommodated.

A chemically treated wick 40 is provided and extends through the entire length of the liner 11 below the inner layer 34. The chemical treatment of this wick is such that when it become moistened, there will be a distinct color change in the same. Thus it can be seen that whenever the wearer of the lined garment of the present invention soils such liner, the wick 40 will change color immediately indicating to attendants or other personnel the need for a change of such liner.

Figure 7:
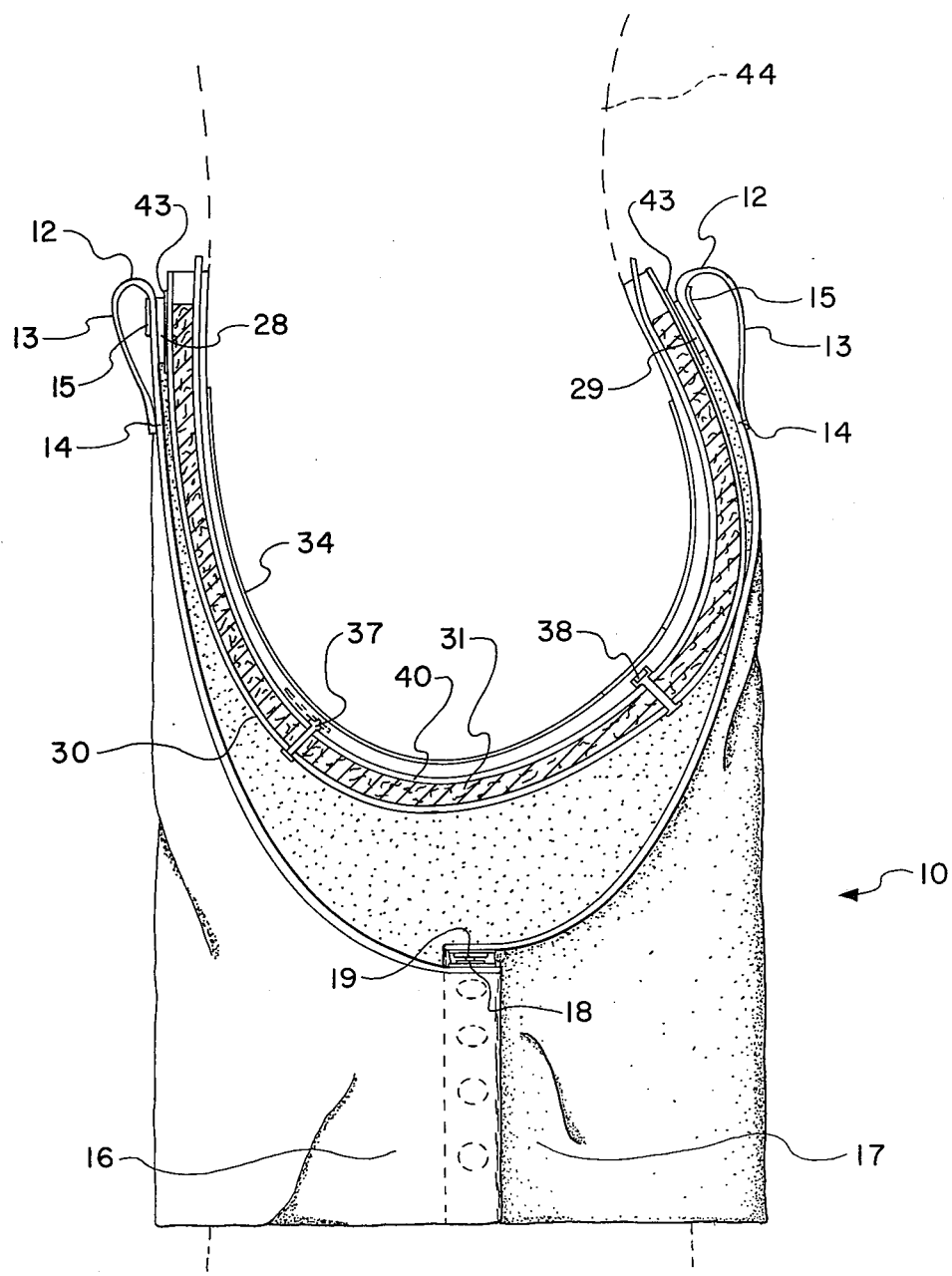
FIG. 7 is a midline sectional view of the incontinent garment and its associated liner in use position.

On the exterior surface of backing 30 adjacent each of the extreme ends 41 and 42 of the liner 11 is provided a liner securing means such as adhesive surfaces 43. These surfaces are adapted to come into contact with appropriate contact areas 28 and 29 to hold the liner 11 in proper relationship with the garment 10 as seen clearly in FIGS. 2, 3 and 7.

In use of the combination incontinent garment and liner of the present invention, any protective layers (not shown) or portions thereof over the adhesive surfaces 43 are removed. The garment 10 is then placed in such a position that the adhesive surfaces 43 at ends 41 or 42 can be placed adhesively juxtaposed to the appropriate contact area 28 or 29.

With very little movement and disturbing of the patient or wearer 44, pad 25 can be slipped under such wearer and the body conforming, comfortable liner 11 passed through the crotch area of such wearer. The garment 10 is then wrapped around the wearer and the remaining adhesive surfaces 43 placed in adhesing contact with the remaining contact surface. The closing of the garment is then a simple matter of securing the connecting surfaces 20 and 21 together and similarly securing connective surfaces 18 and 19 of the crotch area. Finally the draw string 15 can be pulled into snug comfort and tied in a bow or other knot such as seen in FIGS. 2 and 3. A boxer type pair of incontinent shorts are thus provided which are nice looking, protects the modesty of the patient in a sophisticated way, and has a comfortable, large volume of absorbent lining which can accommodate test and monitoring means, devices or apparatus.

When it is desired to remove the garment of the present invention to either change the liner or for whatever reason all that is required is a reversal of the dressing procedure with the draw string 15 being loosened and the side and crotch fasteners released. The adhesive to contact surface securing means can be pulled loose and the liner removed if soiled. If another liner is used to replace the soiled one, it is simply reinserted in the garment as hereinabove described and the garment redressed onto the wearer thereof.

From the above, it can be seen that the present invention provides an economical and yet comfortable and highly absorbent liner for incontinent type persons. Also when combined with the garment of the present invention, a unit is provided which protects the dignity of the wearer by providing a boxer type short rather than a diaper type rubber pant. This garment has the added advantage of providing a pad for reducing or preventing bed sores and which also because of its configuration, aids in retaining the garment in proper wearing position.

The terms "upper", "lower", "sides", "inside", "outside" and so forth have been used herein merely for convenience to describe the combination garment and liner and its parts as oriented in the drawings. It is to be understood, however that these terms are in no way limiting to the invention since it may obviously be disposed in many different positions when in use.

Although various types of fastening and securing means have been described herein, it is to be understood that substitutes or other types of means can obviously be used and it is not intended for the present invention to be limited to those shown or described.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended Claims are intended to be embraced herein.

What is claimed is:

1. A combination incontinent garment and liner comprising: a generally rectangular shaped basic garment; a pair of space arcuate shaped open portions in one end of said garment; means for releasably securing said arcuate portions together when said garment is wearingly wrapped about a wearer thereof; means for releasably fastening together the opposed edges of said garment which are perpendicular to the edge incorporating said arcuate portions; a generally 8-shaped absorbent garment liner to give a greater absorbent area on either side of the crotch with a reduced amount of material being provided in such crotch area; said liner including a generally moisture impervious backing layer, at least one absorbent layer, and a moisture transfer layer; said backing and said absorbent layers being folded into at least one tuck so as to form a moisture retaining reservoir with the moisture transfer layer being unfoldingly disposed thereover whereby a smooth surface is presented to the body of the wearer.

2. The means of claim 1 wherein a tyable draw string is provided within the edge of said garment opposite the edge incorporating said arcuate portions whereby a snug fit around the waist of the wearer can be accomplished.

3. The means of claim 1 wherein padding is provided in said garment in the area adjacent the hips of the wearer.

4. The means of claim 1 wherein said garment is composed of a semi-permanent type of material.

5. The means of claim 1 wherein a moisture reactive wick is provided within said liner whereby when moisture is present an indication to such effect will be given.

6. The means of claim 1 wherein said liner is so constructed as to be at least semi-disposable.

* * * * *